United States Patent
Coman et al.

(10) Patent No.: US 10,126,457 B2
(45) Date of Patent: Nov. 13, 2018

(54) MOTION DETECTION AND CORRECTION OF MAGNETIC RESONANCE DATA

(71) Applicants: Radu Coman, Hannover (DE); Holger Tietjen, Hannover (DE); Martin Blanz, Celle (DE); Holger F. Thern, Hannover (DE)

(72) Inventors: Radu Coman, Hannover (DE); Holger Tietjen, Hannover (DE); Martin Blanz, Celle (DE); Holger F. Thern, Hannover (DE)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 281 days.

(21) Appl. No.: 15/061,636

(22) Filed: Mar. 4, 2016

(65) Prior Publication Data

US 2017/0254919 A1    Sep. 7, 2017

(51) Int. Cl.
*G01V 3/32* (2006.01)
*E21B 49/08* (2006.01)
(Continued)

(52) U.S. Cl.
CPC ............... *G01V 3/32* (2013.01); *E21B 47/12* (2013.01); *E21B 49/00* (2013.01); *E21B 49/08* (2013.01);
(Continued)

(58) Field of Classification Search
CPC .... G01N 24/081; G01R 33/448; G01R 33/36; G01R 33/44; G01R 33/383;
(Continued)

(56) References Cited

U.S. PATENT DOCUMENTS

| | | |
|---|---|---|
| 5,933,006 A | 8/1999 | Rasche et al. |
| 6,268,726 B1 | 7/2001 | Prammer et al. |

(Continued)

FOREIGN PATENT DOCUMENTS

WO    2014160794 A1    10/2014

OTHER PUBLICATIONS

International Search Report and the Written Opinion of the International Searching Authority; PCT/US2017/020375; Korean Intellectual Property Office; dated Jun. 14, 2017; 8 pages.
(Continued)

*Primary Examiner* — Rishi Patel
(74) *Attorney, Agent, or Firm* — Cantor Colburn LLP (57) ABSTRACT

A nuclear magnetic resonance (NMR) apparatus includes a transmitting assembly configured to emit one or more dual-wait-time pulse sequences, and a receiving assembly configured to detect a long-wait-time echo train and a short-wait-time echo train. The apparatus also includes a processor configured to perform at least one of: estimating a difference between the long-wait-time echo train and the short-wait-time echo train to generate a differential echo-train, inverting the differential echo-train into a differential $T_2$ distribution, and detecting a motion artefact in response to determining that the differential echo-train includes a short-$T_2$ porosity fraction that is greater than a threshold value; and inverting two echo trains into two $T_2$ distributions, calculating at least two porosity fractions for each of the two $T_2$ distributions, estimating a shift of a porosity amount between the at least two porosity fractions, and detecting the motion artefact based on the shift.

20 Claims, 4 Drawing Sheets

(51) Int. Cl.
*E21B 47/12* (2012.01)
*E21B 49/00* (2006.01)
*G01N 24/08* (2006.01)
*G01R 33/36* (2006.01)
*G01R 33/383* (2006.01)
*G01R 33/44* (2006.01)

(52) U.S. Cl.
CPC ......... *G01N 24/081* (2013.01); *G01R 33/448* (2013.01); *G01R 33/36* (2013.01); *G01R 33/383* (2013.01); *G01R 33/44* (2013.01)

(58) Field of Classification Search
CPC .. G01R 33/56509; G01R 33/445; G01V 3/32; G01V 3/38; E21B 47/12; E21B 49/00; E21B 49/08
See application file for complete search history.

(56) References Cited

U.S. PATENT DOCUMENTS

| | | | |
|---|---|---|---|
| 6,291,995 B1 | 9/2001 | Speier et al. | |
| 6,331,775 B1 | 12/2001 | Thern et al. | |
| 6,566,874 B1 | 5/2003 | Speier et al. | |
| 7,180,287 B2 | 2/2007 | Rottengatter et al. | |
| 7,196,516 B2 | 5/2007 | Blanz et al. | |
| 7,268,547 B2 | 9/2007 | Kruspe et al. | |
| 7,358,725 B2 | 4/2008 | Blanz | |
| 9,671,483 B2* | 6/2017 | Blanz | G01R 33/56509 |
| 2003/0016013 A1 | 1/2003 | Kruspe et al. | |
| 2005/0248342 A1 | 11/2005 | Rottengatter et al. | |
| 2005/0272158 A1 | 12/2005 | Galford et al. | |
| 2015/0241541 A1 | 8/2015 | Blanz et al. | |
| 2016/0018555 A1* | 1/2016 | Jachmann | G01V 3/32 324/303 |
| 2016/0116629 A1 | 4/2016 | Coman et al. | |
| 2017/0205527 A1* | 7/2017 | Coman | G01V 3/32 |

OTHER PUBLICATIONS

Coates, et al.; NMR Logging Principles & Applications; Halliburton Energy Services Publications; (1999); pp. 1-120.

Coates, et al.; NMR Logging Principles & Applications; Halliburton Energy Services Publications; (1999); pp. 121-233.

Coman, et al.; Improved NMR Logging Approach to Simultaneously Determine Porosity T2 and T1.; 2015; Society of Petroleum Engineers; 27 pages.

Horkowitz, et al., Applications of a New Magnetic Resonance Logging -While-Drilling Tool in a Gulf of Mexico Deepwater Development Project, Retreived on Oct. 24, 2014, SPWLA 43rd Annual Logging Symposium, Jun. 2-5, 2002, 14 pages.

Menger, et al.;"NMR in Motion";(May-Jun. 2003); Petrophysics, vol. 44, No. 3; 6 pages.

\* cited by examiner

MOTION DETECTION AND CORRECTION OF MAGNETIC RESONANCE DATA

BACKGROUND

Understanding the characteristics of geologic formations and fluids located therein is important for effective hydrocarbon exploration and production. Formation evaluation relies on accurate petrophysical interpretation derived from a diverse set of logging technologies. One such technology, nuclear magnetic resonance (NMR), can be used to estimate formation characteristics such as porosity and permeability of rocks, to perform fluid typing and determine fluid volumes, and to estimate fluid characteristics such as viscosity.

Porosity and other properties derived from NMR measurements (e.g., fluid volumetrics, permeability, saturation, viscosity, fluid typing, pore size distribution) can be affected by various motions of an NMR tool. Accounting for such motions is important for acquisition of accurate estimations of formation characteristics based on NMR measurements.

SUMMARY

An embodiment of a nuclear magnetic resonance (NMR) apparatus for estimating properties of an earth formation includes a carrier configured to be deployed in a borehole in the earth formation, a nuclear magnetic resonance (NMR) measurement device including a transmitting assembly configured to emit one or more dual-wait-time pulse sequences, and a receiving assembly configured to detect a long-wait-time echo train and a short-wait-time echo train based on the one or more dual-wait-time pulses sequences. The NMR apparatus also includes a processor configured to analyze the long-wait-time echo train and the short-wait-time echo train to detect a potential motion artefact related to a magnetic field variation in a volume of interest. The processor is configured to perform at least one of: estimating a difference between the long-wait-time echo train and the short-wait-time echo train to generate a differential echo-train, inverting the differential echo-train into a differential $T_2$ distribution, and detecting the motion artefact in response to determining that the differential echo-train includes a short-$T_2$ porosity fraction that is greater than a threshold value; and inverting two echo trains into two $T_2$ distributions, the two echo trains selected from the long-wait-time echo train, the short-wait-time echo train and the differential echo train, calculating at least two porosity fractions for each of the two $T_2$ distributions, estimating a shift of a porosity amount between the at least two porosity fractions, and detecting the motion artefact based on the shift.

An embodiment of a method of performing a nuclear magnetic resonance (NMR) measurement includes receiving NMR measurement data including a long-wait-time echo train and a short-wait-time echo train, the measurement data generated by a nuclear magnetic resonance (NMR) measurement device disposed in a carrier in an earth formation, the NMR measurement device including a transmitting assembly configured to emit one or more dual wait time pulse sequences into a formation volume of interest, and analyzing the long-wait-time echo train and the short-wait-time echo train by a processor to detect a potential motion artefact related to a magnetic field variation in the volume of interest. Analyzing includes at least one of: estimating a difference between the long-wait-time echo train and the short-wait-time echo train to generate a differential echo-train, inverting the differential echo-train into a differential $T_2$ distribution, and detecting the motion artefact in response to determining that the differential echo-train includes a short-$T_2$ porosity fraction that is greater than a threshold value; and inverting two echo trains into two $T_2$ distributions, the two echo trains selected from the long-wait-time echo train, the short-wait-time echo train and the differential echo train, calculating at least two porosity fractions for each of the two $T_2$ distributions, estimating a shift of a porosity amount between the at least two porosity fractions, and detecting the motion artefact based on the shift.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Methods, systems and apparatuses for measuring characteristics of an earth formation using magnetic resonance techniques are described herein. Embodiments of nuclear magnetic resonance (NMR) apparatuses, systems and methods utilize dual-wait-time (DTW) pulse sequences to estimate and/or correct for motion. As described herein, "motion" refers to any condition that can cause instability of a magnetic field or otherwise affect the magnetic field in such a way as to affect NMR measurements. This instability can be caused by mechanical motion or by another condition, such as sub-optimal performance of an NMR tool. Embodiments described herein are useful for correction of NMR measurement errors due to various types of motions of an NMR tool or other downhole component, such as axial motion and lateral motion (including lateral vibrations), and for errors due to an imperfect or sub-optimal (e.g., not axisymmetric) $B_0$ field or $B_1$ field stability.

An embodiment of an NMR apparatus or system is configured to perform an NMR measurement by emitting DTW pulse sequences that include a first pulse sequence having a first wait time and a second pulse sequence having a second wait time into a formation volume of interest. "Wait time" is defined, in one embodiment, as the time during which the NMR-active material (earth formation) is polarized, i.e. magnetized. A receiving assembly is configured to detect a long-wait-time echo train based on the first pulse sequence and a short-wait-time echo train based on the second pulse sequence. The NMR apparatus or system includes a processor that is configured to estimate formation properties including volumes of fluid within a formation volume of interest. The processor is also configured to estimate and/or correct for motion by detecting shifts in detected volumes of partial porosities in the formation volume of interest. For example, the processor detects motion by determining a shift of a portion of the porosity in a $T_2$ distribution from a long-$T_2$ porosity to a short-$T_2$ porosity. This shift is also referred to as a "motion artefact". It is noted that the terms "first" and "second" are not intended to imply a temporal order.

Figure 1:
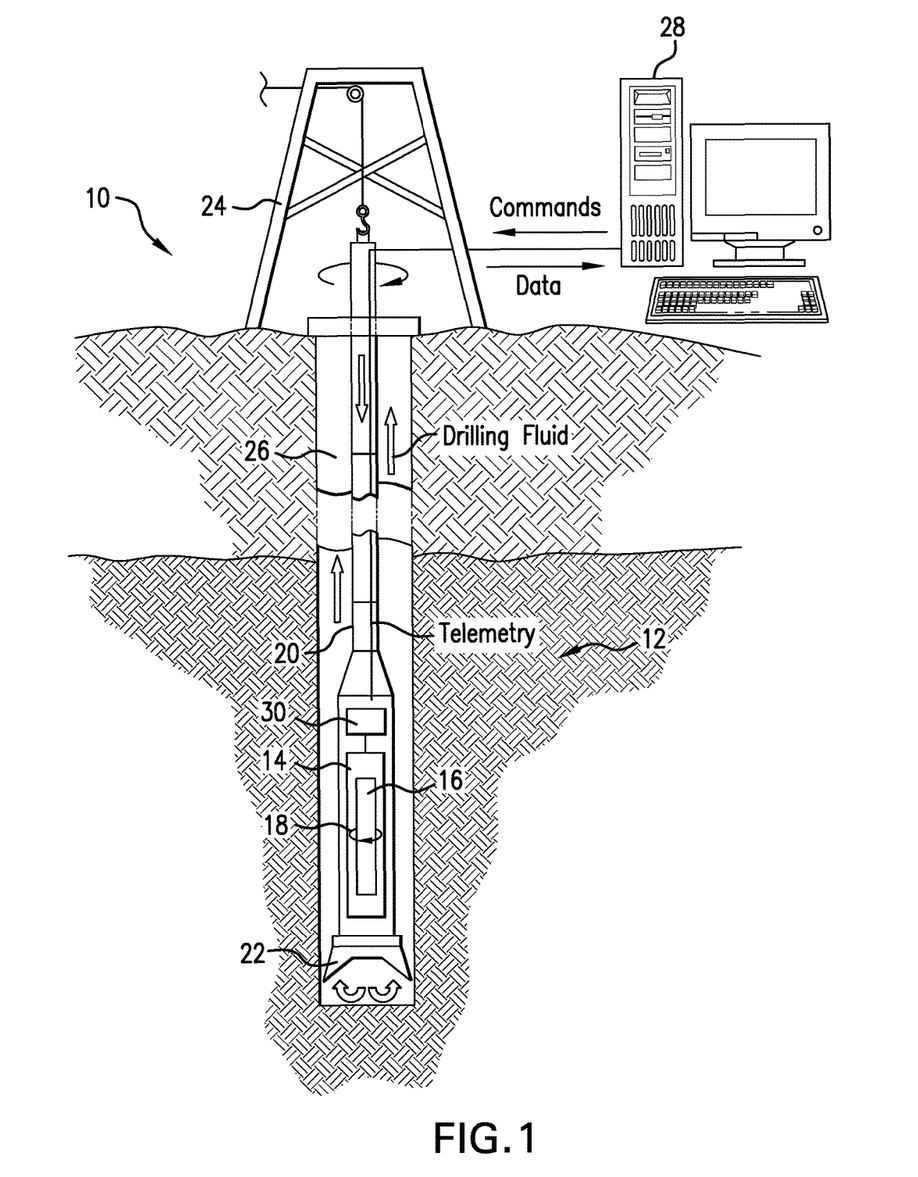
FIG. 1 depicts an embodiment of a formation measurement system that includes a nuclear magnetic resonance (NMR) measurement apparatus.

FIG. 1 illustrates an exemplary embodiment of a downhole measurement, data acquisition, and/or analysis system 10 that includes devices or systems for in-situ measurement of characteristics of an earth formation 12. The system 10 includes a magnetic resonance apparatus such as an NMR tool 14. An example of the magnetic resonance apparatus is a logging-while-drilling (LWD) magnetic resonance tool. The tool 14 is configured to generate magnetic resonance data for use in estimating characteristics of a formation, such as porosity, irreducible water saturation, permeability, hydrocarbon content, and fluid viscosity.

An exemplary tool 14 includes a static magnetic field source 16, such as a permanent magnet assembly, that magnetizes formation materials and a transmitter and/or receiver assembly 18 (e.g., an antenna or antenna assembly) that transmits radio frequency (RF) energy or pulsed energy that provides an oscillating magnetic field in the formation, and detects NMR signals as voltages induced in the receiver. The transmitter assembly 18 may serve the receive function, or distinct receiving antennas may be used for that purpose. It can be appreciated that the tool 14 may include a variety of components and configurations as known in the art of nuclear magnetic resonance or magnetic resonance imaging.

The tool 14 may be configured as a component of various subterranean systems, such as wireline well logging and LWD systems. For example, the tool 14 can be incorporated within a drill string 20 including a drill bit 22 or other suitable carrier and deployed downhole, e.g., from a drilling rig 24 into a borehole 26 during a drilling operation. The tool 14 is not limited to the embodiments described herein, and may be deployed in a carrier with alternative conveyance methods. A "carrier" as described herein means any device, device component, combination of devices, media and/or member that may be used to convey, house, support or otherwise facilitate the use of another device, device component, combination of devices, media, and/or member. Exemplary non-limiting carriers include drill strings of the coiled tube type, of the jointed pipe type, and any combination or portion thereof. Other carrier examples include casing pipes, wired pipes, wirelines, wireline sondes, slickline sondes, drop shots, downhole subs, bottom-hole assemblies, and drill strings.

In one embodiment, the tool 14 and/or other downhole components are equipped with transmission equipment to communicate ultimately to a surface processing unit 28. Such transmission equipment may take any desired form, and different transmission media and methods may be used, such as wired, fiber optic, mud pulse telemetry and/or other wireless transmission methods. Additional processing units may be deployed with the carrier. For example, a downhole electronics unit 30 includes various electronic components to facilitate receiving signals and collect data, transmitting data and commands, and/or processing data downhole. The surface processing unit 28, electronics 30, the tool 14, and/or other components of the system 10 include devices as necessary to provide for storing and/or processing data collected from the tool 14 and other components of the system 10. Exemplary devices include, without limitation, at least one processor, storage, memory, input devices, output devices, and the like.

Magnetic resonance measurements are performed by the NMR tool 14, which generates a static magnetic field ($B_0$) in a volume within the formation (a "volume of interest") using one or more magnets (e.g., the magnetic field source 16). An oscillating (e.g., RF) magnetic field ($B_1$) is generated, which is at least substantially perpendicular to the static magnetic field in the volume of interest. The volume of interest may be circular or toroidal around the borehole, and/or focused or directed toward a specific angular region (i.e., side-looking).

The surface processing unit 28, electronics 30 and/or other suitable processing device includes a processor configured to generate electrical pulses and transmit the pulses to the transmitter assembly, which in turn generates pulses of electromagnetic energy that induce the oscillating field $B_1$ in the volume of interest. Such a processing device may be referred generally as a pulse generator, which includes a microcontroller or other processor that is capable of transmitting a pulse sequence or series of pulse sequences. Each pulse sequence can be programmed or set based on parameters such as pulse duration, time intervals between pulses and time between successive pulse sequences (wait time).

When exposed to the magnetic field $B_0$, the spin axes of hydrogen nuclei in the formation precess around the direction of the $B_0$ field with the Larmor frequency, which is proportional to the strength of the magnetic field $B_0$. The direction of orientation of the field $B_0$ in the formation volume of interest is referred to as the longitudinal direction or z-direction.

Over time, the spin axes align themselves at distinct angles along the $B_0$ field and create a net magnetization (i.e., polarization), which will build up with the time constant $T_1$, referred to as a longitudinal relaxation or spin lattice relaxation time. $T_2$ is a time constant of the transversal relaxation, which describes the loss of magnetization in the plane orthogonal to the $B_0$ field.

When the $B_1$ field is turned on, the magnetization will be rotated around the $B_1$ field by an angle proportional to the length of the pulse and to the strength of the $B_1$ field. Ideally, the $B_1$ field is oriented perpendicular to the $B_0$ field in the volume of interest, e.g., in the x-y plane orthogonal to the longitudinal or z-axis, where the z-axis points along $B_0$ in the volume of interest.

The $B_1$ field is typically applied as a sequence of short-duration pulses, referred to as a "pulse sequence" or "data gathering sequence". The said pulses may be rectangular or other shaped. A pulse sequence is used to measure $T_2$ relaxation, and is also indirectly used for the measurement of the $T_1$ relaxation. In an embodiment of a pulse sequence, the first pulse is a "tipping pulse", which acts to align the nuclear magnetization in the formation in a direction perpendicular to the static field $B_0$, e.g., rotate the magnetization from the z-direction into the x-y plane. After the tipping pulse, the nuclear magnetization disperses in the x-y plane due to a spread of precession frequencies caused by $B_0$ field inhomogeneity and gradually returns or "relaxes" to its alignment with the static field.

At a selected time after the tipping pulse, one or more "refocusing pulses" are applied, which have a duration and amplitude selected to at least partly reverse the magnetizations of microscopic volume elements. In consequence the coherent macroscopic magnetization that was lost after the tipping pulse rephases after each refocus pulse, resulting in so-called spin echoes that induce a measurable voltage in the receiving antenna.

The refocus pulses restore only the transversal magnetization that gets lost due to the inhomogeneity of the $B_0$ field.

The loss of magnetization due to relaxation processes cannot be restored and will happen with a time $T_2$.

Pulse sequence parameters include wait time (TW), echo spacing or inter-echo time (TE), the number of echoes ($N_E$) produced by a sequence, and the number of successive repeated pulse sequences. The wait time is the period of time between a saturation sequence (which is performed for deleting magnetization in the formation) and the onset of the first pulse of an NMR echo detection sequence or the period of time between successive NMR echo detection sequences. Nuclear magnetization of the volume of interest recovers during the wait time. After a pulse sequence, the nuclear magnetization is more or less zero and another wait time is used to re-establish the magnetization prior to application of the next sequence.

Parameters may be selected based on considerations such as anticipated formation properties and anticipated fluid types and properties. TW can be selected to measure different formation types and regions expected to have different $T_1$ ranges. For example, longer TWs, usually in connection with a larger number of echoes, are useful for movable or non-wetting fluids.

An example of a pulse sequence that can be applied by the NMR tool is a Carr-Purcell-Meiboom-Gill (CPMG) pulse sequence, which has a constant time $2*\tau=TE$ between the refocus pulses, where "$\tau$" is approximately the time between the tipping pulse and the first refocusing pulse. Note that, for a CPMG pulse sequence, the inter-pulse time interval is the same as the inter-echo time interval, TE, where TE is measured between centers of echoes or centers of refocus pulses.

Systems and/or processors described herein are configured to perform various functions including performing NMR measurements and/or estimating formation properties, as well as detecting and/or correcting for motion. A processor is configured to perform NMR methods and account for effects of motion on NMR measurements, such as enhanced decay of the recorded amplitude of the echoes. For example, in the presence of a free fluid with long $T_2$ values (e.g., low viscosity or light oil), motion of the NMR tool 14 or other carrier leads to a partial shift of detected porosity from a long-$T_2$ fluid volumetric to a short-$T_2$ fluid volumetric. The value of the additional porosity resulting from this shift is proportional to a polarized measured long-$T_2$ porosity.

With respect to NMR logging, multiple types of motion of downhole components may occur. One type of motion is axial motion (along the axis of a borehole) with slowly varying velocity, which is the logging speed in wireline applications or rate of penetration (ROP) in while-drilling applications. Another type of motion includes fast small-range movements, which typically represent a small deflection (e.g., on the order of millimeters. Thus type of motion includes axial motions (e.g., axial vibrations) and lateral motions (e.g., lateral vibrations).

In one embodiment, corrections of NMR measurements are performed to compensate for vibrations or other small-range motions, which can be axial, lateral or have both axial and lateral components. The effect of these motions on the NMR signals is generally caused by magnetic fields that move with respect to a fixed location in the formation from where the NMR signals originate. For this reason, the rotation of an axi-symmetric NMR tool with a non-perfect axi-symmetric magnet field can also affect NMR signals. Thus, even an instability of a magnetic field or instability of a magnetic field amplitude may be considered motion, regardless whether that instability is caused by mechanical motion or electronic instability of a magnetic field generator.

The effect of a non-axisymmetric $B_0$ field on NMR data is similar to the effect of lateral motion.

In one embodiment, the processor uses a dual-wait-time (DTW) measurement and estimates the above mentioned shift of detected porosity to estimate motion by detecting and/or measuring motion artefacts, and may also use the estimated motion to correct properties derived from NMR measurements, such as porosity. In a DTW configuration, a transmitting assembly is configured to emit pulse sequences that include at least a first pulse sequence having a first wait time and a second pulse sequence having a second wait time into a formation volume of interest. A receiving assembly detects echo trains (referred to herein as "long-wait-time echo trains") based on the first pulse sequence, and also detects echo trains (referred to herein as "short-wait-time echo trains") based on the second pulse sequence.

Figure 2:
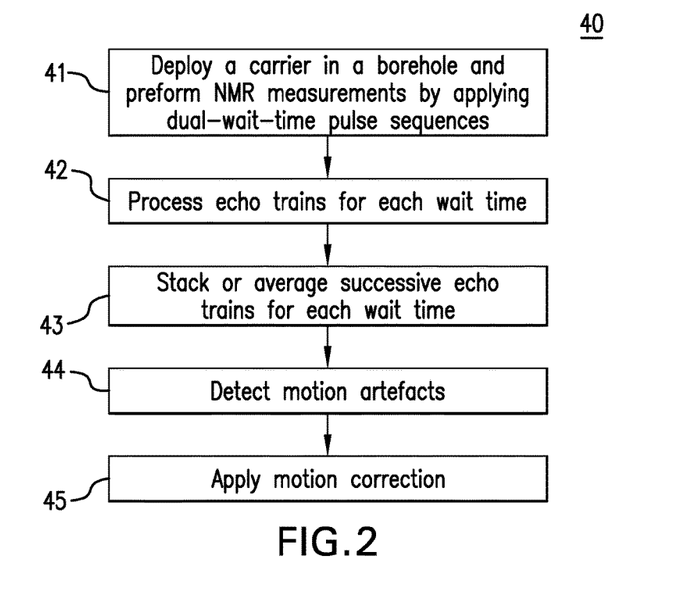
FIG. 2 is a flow chart that depicts an embodiment of a NMR measurement method that includes estimating and/or correcting for motion using dual-wait-time pulse sequences.

FIG. 2 illustrates a method 40 for performing an NMR measurement operation that includes estimation of motion and/or correction of NMR data based on estimations of motion. The method 40 may be performed in conjunction with the system 10, but is not limited thereto. The method 40 includes one or more of stages 41-45 described herein, at least portions of which may be performed by a processor (e.g., the surface processing unit 28). In one embodiment, the method 40 includes the execution of all of stages 41-45 in the order described. However, certain stages 41-45 may be omitted, stages may be added, or the order of the stages changed.

In the first stage 41, an NMR or other magnetic resonance measurement tool is deployed into a borehole. In one embodiment, the tool (e.g., the tool 14) is deployed as part of a wireline operation, or during drilling as part of an LWD operation. The speed at which the NMR device is advanced is referred to as logging speed.

Measurements are performed by generating a static magnetic field $B_0$ in a volume of interest in the formation, and transmitting a pulsed signal from at least one transmitting antenna according to at least two different pulse sequences, which in turn generate an oscillating magnetic field $B_1$ in the volume of interest. At least one receiving antenna detects NMR signals from the volume in response to the interaction between the nuclear spins of interest and the static and oscillating magnetic fields, and generates raw NMR data. The raw NMR data include spin echo trains that may be measured at a plurality of depths. In one embodiment, the pulse sequences are CPMG pulse sequences.

Output from each measurement is detected as time domain amplitude measurements generated by each pulse sequence. The time domain amplitude values for a pulse sequence are referred to as an echo train, in which the echo amplitude decreases with the time constant $T_2$. The decrease may be exponential (e.g., in the case of a unimodal decay with no motion), multi exponential (i.e. a sum of exponentials), or non-exponential (e.g., in the presence of axial or lateral motion).

In one embodiment, the measurements are performed by emitting a plurality of pulse sequences that include at least two sequences, each having a different wait time ("TW"). The at least two sequences in this embodiment are referred to as dual-wait-time ("DTW") sequences. The DTW sequences include a first sequence having a relatively long wait time and a second sequence having a relatively short wait time. The first sequence is referred to as a "long-TW sequence" having a long wait time ($TW_L$), and the second sequence is referred to as a "short-TW sequence" (having a short wait time ($TW_S$) relative to the first sequence.

The wait times may be selected based on the $T_1$ time for a given volumetric component (or simply volumetric) of the volume of interest, i.e., the time needed to polarize a fluid or formation material. Examples of volumetrics include heavy oil, light hydrocarbons (e.g., gas and/or light oil), free fluid, moveable water, bound fluids, clay bound water and capillary bound water. In one embodiment, if saturation sequences are used, the wait time is the time from the end of a saturation sequence to the first pulse (tipping pulse) of the following CPMG sequence. In one example, $TW_L > 3 * T_{1,LHC}$, where $T_{1,LHC}$ is the log-mean (or geometric mean) $T_1$ for a light hydrocarbon (e.g., gas and/or light oil) volumetric. $TW_S > 3 * T_{1,MW}$, where $T_{1,MW}$ is the log-mean $T_1$ for a movable water volumetric. Various rules may be used for selection of the relative wait times for the $TW_L$ sequence and the $TW_S$ sequence. Any suitable criteria may be used to select the relative wait times, such as the desired resolution (e.g., vertical resolution) and motion characteristics (e.g., motion frequency).

In one embodiment, at least one sequence is configured as a phase-alternate pair (PAP) sequence pattern. A PAP sequence pattern includes two consecutively recorded sequences, where the phase of the tipping pulse of the second sequence in the pair being reversed relative to the phase of the tipping pulse of the first sequence in the pair. The echoes of the two consecutive sequences are subtracted to eliminate ringing and offset. In this embodiment, the $TW_L$ sequence includes two phase alternating paired (PAPed) sequences, and the $TW_S$ sequence includes also two PAPed sequences.

The DTW measurement may also include a clay bound water (CBW) measurement which includes one or more CBW sequences. A CBW sequence is a sequence having a wait time corresponding to the $T_1$ value for clay bound water.

For example, a long measurement is performed by detecting echo trains from a $TW_L$ sequence, and a short measurement is performed by detecting echo trains from a $TW_S$ sequence. Optionally, an additional measurement is performed using a CBW sequence having a wait time that is shorter than both the long and short wait times. If PAPs are used, the $TW_L$ sequence may include one PAP or multiple PAPs, and the $TW_S$ sequence and the CBW sequence may include multiple PAPs.

In the second stage 42, measured data including raw echo trains are processed to, e.g., remove noise and improve analysis. For example, processing includes an optional despiking (spike noise removal) of the measured data. Another example of processing includes calibration to correlate data values with fluid and/or formation property values. For example, the measured data (spin echo trains) are multiplied by a calibration factor to transform arbitrary units into porosity units. Other processing techniques include, for example, filtering to remove incomplete measurements, and phase rotating the data into a "signal channel".

An optional outflow correction may be applied to the processed NMR data. In one embodiment, an "outflow correction" corresponds to the "motion correction A" described in U.S. Pat. No. 7,358,725, which is incorporated herein by reference in its entirety. The outflow correction might be due to axial and/or radial movement of the tool. In one embodiment, the outflow correction can be applied on phase rotated PAPed echo trains. Alternatively the order of this stage and of the next stage ("stack and average echo trains") might be interchanged and the outflow correction would be applied on the stacked or averaged echo trains.

In the third stage 43, in one embodiment, the first pulse sequence includes a first plurality of successive echo trains detected from a plurality of successive pulse sequences having the first wait time, and the second pulse sequence includes a second plurality of successive pulse sequences having the second wait time. The processor is configured to stack or average the first plurality of successive echo trains to generate the long-wait-time echo train, and stack or average the second plurality of successive echo trains to generate the short-wait-time echo train.

Figure 3:
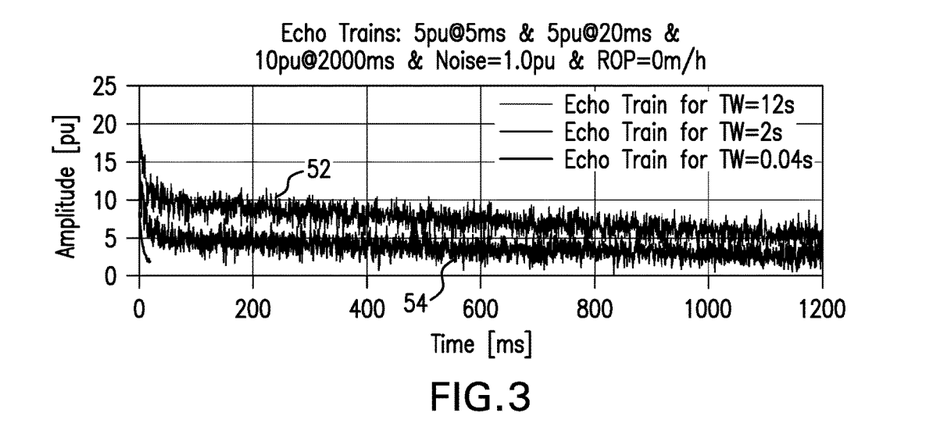
FIG. 3 depicts an example of echo trains generated by dual-wait-time pulse sequences.

For example, successive echo trains received during NMR measurements are stacked or averaged in a "running average" fashion to improve the signal-to-noise ratio. Multiple sequences having a selected TW are generated and a running average of the echo trains detected from each sequence is calculated to produce a combined echo train. FIG. 3 shows an example of two simulated combined or stacked echo trains 52, 54. Echo train 52 is for a TW of 12 seconds and train 54 is for a TW of 2 seconds.

In the fourth stage 44, the echo trains are analyzed to detect potential motion artefacts that are related to magnetic field variation. Motion artefacts are caused, as discussed above, by movement or vibration of the NMR tool, changes or errors in a magnetic field source, or other conditions that result in magnetic field variations.

In one embodiment, motion artefacts are detected in conjunction with a differential echo train by estimating a difference between the long-wait-time echo train and the short-wait-time echo train to generate a differential echo train. For example, amplitude values of individual echoes from the short-wait-time echo train are subtracted from corresponding amplitude values of the long-wait-time echo train.

The differential echo train is then inverted to transform the data from the time domain (echo train data) into the $T_2$ domain ($T_2$ distribution). The inversion results in a differential $T_2$ distribution.

The differential $T_2$ distribution is divided into two or more volume fractions, or fractions of the pore space volume. Each volume fraction is associated with a $T_2$ value range. For example, the differential $T_2$ distribution is divided into two volumetrics: a fraction of the pore space fluid volume or volume fraction associated with short-$T_2$ values (referred to as a "short-$T_2$" fluid or a "short-$T_2$ porosity fraction"), and a fraction of the pore space fluid volume or volume fraction associated with long-$T_2$ values (referred to as a "long-$T_2$" fluid or a "long-$T_2$ porosity fraction"). Short-$T_2$ fluids are fluids or combinations of fluids corresponding to $T_2$ values or a portion of a $T_2$ distribution below a selected threshold or cutoff, and long-$T_2$ fluids are fluids corresponding to $T_2$ values or a portion of a $T_2$ distribution at or above the cutoff.

To detect whether a motion artefact exists, the short-$T_2$ porosity fraction is compared to a threshold value. In one embodiment, a motion artefact is detected if the short-$T_2$ porosity fraction is equal to or greater than a threshold value. For example, If the short-$T_2$ porosity fraction of the differential T2 distribution is larger than a threshold (e.g., 1 porosity unit or alternatively 3% of total porosity), then a motion artefact is detected.

This embodiment of detecting motion artefacts using the differential $T_2$ distribution is advantageous, in that detection can be performed using only a single $T_2$ distribution and one porosity fraction (the differential short-$T_2$ porosity).

In one embodiment, the echo train data are inverted to transform the data from the time domain (echo train data) into the $T_2$ domain ($T_2$ distribution) and generate at least two $T_2$ distributions. The two $T_2$ distributions may include a first $T_2$ distribution for the $TW_L$ sequence (a "$TW_L$ distribution") a second $T_2$ distribution for the $TW_S$ sequence (a "$TW_S$ distribution) and/or the differential $T_2$ distribution. One or more cutoffs (i.e., time values) may be selected to separate a $T_2$ distribution into different volumetrics. In one example, the two $T_2$ distributions are selected as the $TW_L$ distribution and the $TW_S$ distribution. In another example, the two $T_2$ distributions are selected as the $TW_L$ distribution and the differential distribution.

Figure 4:
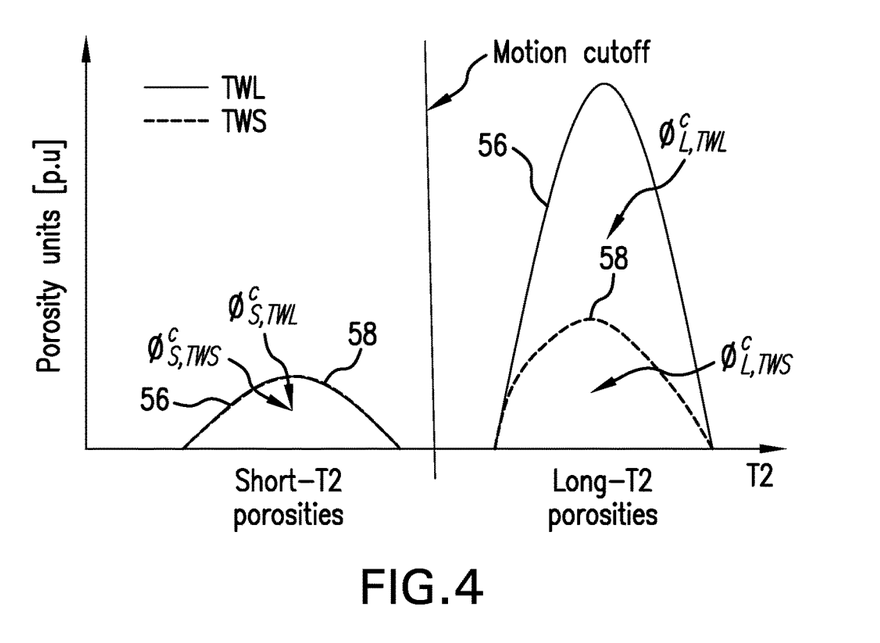
FIG. 4 depicts an example of $T_2$ distribution curves calculated by inverting echo trains generated by dual-wait-time pulse sequences.
Figure 5:
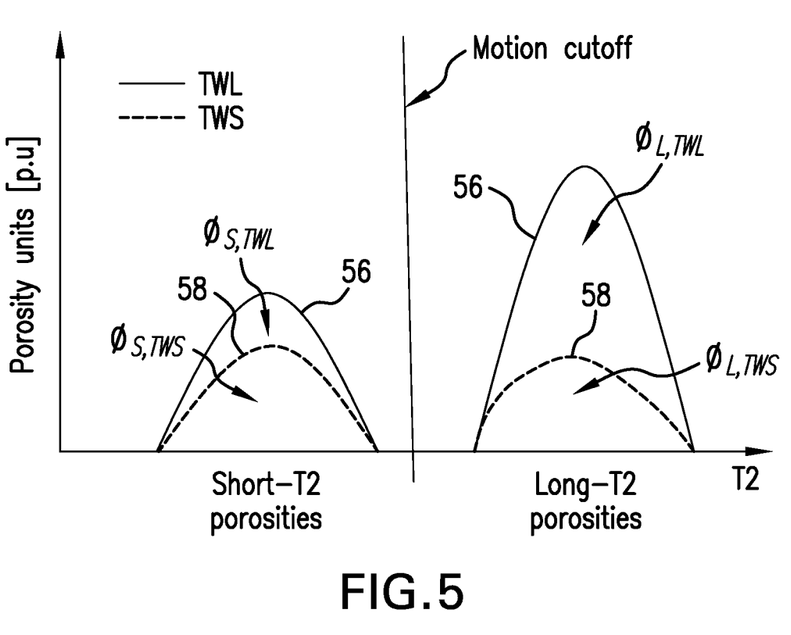
FIG. 5 depicts an example of the $T_2$ distribution curves of FIG. 4 as affected by motion.

An example of $T_2$ distributions calculated based on the $TW_L$ sequence and the $TW_S$ sequence is shown in FIG. 4 (for NMR acquisition that is not affected by motion) and in FIG. 5 (for NMR acquisition that is affected by motion). In this example, the $T_2$ distribution for $TW_L$ is represented by a curve 56, and the $T_2$ distribution for $TW_S$ is represented by a curve 58. The area under each curve may be associated with all or part of the total porosity of the volume of interest, which can be divided by cutoffs to define partial porosities of different volumetrics. FIG. 4 shows examples of a cutoff used to define partial porosities for different volumetrics.

For example, a cutoff (referred to as a "motion cutoff") splits the $T_2$ porosity distribution into two volumetrics: a short-$T_2$ porosity fraction associated with short-$T_2$ fluid, and a long-$T_2$ porosity fraction associated with long-$T_2$ fluid. Short-$T_2$ fluids are fluids or combinations of fluids corresponding to $T_2$ values or a portion of a $T_2$ distribution below a selected threshold or cutoff, and long-$T_2$ fluids are fluids corresponding to $T_2$ values or a portion of a $T_2$ distribution at or above the cutoff. In one embodiment, long-$T_2$ fluids include free fluids (e.g., gas and/or light oil) and short-$T_2$ fluids include bound fluids (e.g., bound water). For example, in some instances, the short-$T_2$ porosity fluid volumetric corresponds to the Bulk Volume Irreducible (BVI) volumetric, and the long-$T_2$ porosity fluid volumetric corresponds to the Bulk Volume Moveable (BVM) volumetric. In such instances, the motion cutoff may be the same or similar to the BVI cutoff, but is not so limited. In one embodiment, the cutoff between short and long-$T_2$ fluids is determined in the laboratory with NMR measurements on core samples. In the absence of laboratory data, default values based on lithology or other information may be used.

FIGS. 4 and 5 illustrate the effect of lateral motion (or other types of motion) or $B_0$ field instability on the measured partial porosity of the long-$T_2$ and short-$T_2$ porosity fractions. A portion of the partial porosity of the long-$T_2$ porosity fraction for the long wait time and for the short wait time is shifted to the partial porosity of the short-$T_2$ porosity fraction. This is shown as a decrease in the volume under the curve 56 and the curve 58 in the long-$T_2$ porosity (above the motion cutoff), and a corresponding increase in the volume under the curve 56 and the curve 58 in the short-$T_2$ porosity (below the motion cutoff).

NMR simulations have shown that lateral motion typically leads to a shift of partial porosity from the long-$T_2$ porosity into the short-$T_2$ porosity. The shifted amount of porosity is proportional to the polarized long-$T_2$ porosity.

Examples of the detection of motion artefacts and motion correction are described below in conjunction with the examples shown in FIGS. 4 and 5. It is noted that the shape, values and shift in partial porosities of FIGS. 4 and 5 are provided for illustration purposes and are not intended to be limiting. Furthermore, the examples can be performed with any suitable pair of $T_2$ distributions, such as a $TW_L$ distribution and a differential $T_2$ distribution.

FIG. 4 shows the partial porosities for NMR measurements that are not affected by motion or that have been corrected for motion as described herein. FIG. 5 shows the partial porosities from NMR measurements that were affected by motion but have not been corrected ("uncorrected partial porosities").

The shift can be associated with a factor of proportionality $\beta$ between the shifted porosity and the long-$T_2$ porosity that is unaffected by motion. The porosity that is missed in the long-$T_2$ porosity (due to the shift of the porosity from the long-$T_2$ to the short-$T_2$ porosity) can be equated to the porosity added into the short-$T_2$ porosity as follows:

$$\beta * \phi_{L,TWL}^c = \phi_{S,TWL} - \phi_{S,TWL}^c, \quad (1)$$

$$\beta * \phi_{L,TWS}^c = \phi_{S,TWS} - \phi_{S,TWS}^c, \quad (2)$$

where $\phi_{S,TWL}$ and $\phi_{S,TWS}$ are measured uncorrected short-$T_2$ porosities from the long and short sequence, respectively, and $\phi_{S,TWL}^c$ and $\phi_{S,TWS}^c$ are the short-$T_2$ porosities corrected for motion. $\phi_{L,TWL}^c$ and $\phi_{L,TWS}^c$ are the long-$T_2$ porosities corrected for motion.

The long-$T_2$ porosities $\phi_{L,TWL}$ and $\phi_{L,TWS}$ that are measured are the parts of the long-$T_2$ porosities that were not shifted. These porosities can be calculated as:

$$\phi_{L,TWL} = (1-\beta) * \phi_{L,TWL}^c, \quad (3)$$

$$\phi_{L,TWS} = (1-\beta) * \phi_{L,TWS}^c, \quad (4)$$

From the above equations, the following equations follow:

$$\phi_{L,TWL}^c = \frac{\phi_{L,TWL}}{1-\beta}, \quad (5)$$

$$\phi_{L,TWS}^c = \frac{\phi_{L,TWS}}{1-\beta}. \quad (6)$$

Inserting equations (5) and (6) into equations (1) and (2) results in the following:

$$\frac{\beta}{1-\beta} * \phi_{L,TWL} = \phi_{S,TWL} - \phi_{S,TWL}^c,$$

$$\frac{\beta}{1-\beta} * \phi_{L,TWS} = \phi_{S,TWS} - \phi_{S,TWS}^c.$$

The above equations are related to a factor of proportionality $\alpha$ between the long-$T_2$ porosity that was shifted and the uncorrected long-$T_2$ porosity, which can be represented by:

$$\alpha = \frac{\beta}{1-\beta}.$$

Thus, we have:

$$\alpha * \phi_{L,TWL} = \phi_{S,TWL} - \phi_{S,TWL}^c,$$

$$\alpha * \phi_{L,TWS} = \phi_{S,TWS} - \phi_{S,TWS}^c,$$

where $\phi_{S,TWL}$ and $\phi_{S,TWS}$ are measured short-$T_2$ porosities and $\phi_{S,TWL}^c$ and $\phi_{S,TWS}^c$ are the motion-corrected short-$T_2$ porosities. Combining the two equations to eliminate the unknown $\alpha$ results in:

$$\frac{\phi_{L,TWL}}{\phi_{L,TWS}} = \frac{\phi_{S,TWL} - \phi_{S,TWL}^c}{\phi_{S,TWS} - \phi_{S,TWS}^c},$$

By considering that:

$$\phi_{S,TWL}^c = P_{S,TWL} * \phi_S^c, \text{ and}$$

$$\phi_{S,TWS}^c = P_{S,TWS} * \phi_S^c, \text{ and}$$

where $P_{S,TWL}$ is the polarization of the short-$T_2$ porosity at a wait time of $TW_L$ and $P_{S,TWS}$ is the polarization of the short-$T_2$ porosity at a wait time of $TW_S$, the polarized short-$T_2$ porosity $\phi_S^c$ corrected for motion can be represented as:

$$\phi_S^c = \frac{\phi_{L,TWL} * \phi_{S,TWS} - \phi_{L,TWS} * \phi_{S,TWL}}{P_{S,TWS} * P_{L,TWL} - P_{S,TWL} * \phi_{L,TWS}}.$$

and the long-$T_2$ porosity corrected for motion becomes:

$$\phi_{L,TWL}^c = \phi_{L,TWL} + \phi_{S,TWL} - P_{S,TWL} * \phi_S^c,$$

$$\phi_{L,TWS}^c = \phi_{L,TWS} + \phi_{S,TWS} - P_{S,TWS} * \phi_S^c,$$

For a typical DTW activation, the short-$T_2$ porosity is assumed to be fully polarized (i.e., $P_{S,TWL} \cong 1$ and $P_{S,TWS} \cong 1$). If $TW_S$ is not sufficiently long to polarize the short-$T_2$ porosity, the polarization of the short-$T_2$ porosity can be estimated by using the $T_2$ distribution and an assumed $T_1/T_2$ ratio. In principle the same applies also if $TW_L$ is not long enough to fully polarize the short-$T_2$ porosity, but is unlikely in practice.

It is noted that the above descriptions and formulas are not intended to be limiting, as various alternative implementations that include comparison of porosity fractions may be utilized. For example, the order of the steps described above for deriving particular terms can be changed, which leads to different formulas. In addition, whether a polarization factor is used or not (or is assumed to be equal to one) opens further options to rewrite the above formulas.

In one embodiment, the shift calculated according to the above methods can be used to estimate the movement (e.g., lateral movement or shift) of an NMR tool or other carrier. The calculated shift can be correlated with motion by any suitable method. For example, experimental and/or empirical data, such as lab data, measured data from other operations and models can be used to calibrate the processor and provide estimations of movement based on the calculated shifts.

In the fifth stage 45, motion correction is applied to compensate for shifts in NMR data that result from motion. For example, by applying the above formulas, a partial porosity is shifted to compensate for shifts due to lateral motion or other types of motion, and/or for instabilities in the $B_0$ or $B_1$ fields.

The apparatuses, systems and methods described herein provide numerous advantages. The embodiments described herein provide an effective technique for correcting errors or shifts in NMR measurements due to lateral motion, such as vibration, as well as imperfections in magnet setup. In addition, motion estimation and/or correction can be achieved using only the NMR measurements without requiring additional measurements or processing capabilities.

Set forth below are some embodiments of the foregoing disclosure:

Embodiment 1

A nuclear magnetic resonance (NMR) apparatus for estimating properties of an earth formation, the apparatus comprising: a carrier configured to be deployed in a borehole in the earth formation; a nuclear magnetic resonance (NMR) measurement device including a transmitting assembly configured to emit one or more dual wait time pulse sequences, and a receiving assembly configured to detect a long-wait-time echo train and a short-wait-time echo train based on the one or more dual-wait-time pulses sequences; and a processor configured to analyze the long-wait-time echo train and the short-wait-time echo train to detect a potential motion artefact related to a magnetic field variation in the volume of interest, the processor configured to perform at least one of: estimating a difference between the long-wait-time echo train and the short-wait-time echo train to generate a differential echo-train, inverting the differential echo-train into a differential $T_2$ distribution, and detecting the motion artefact in response to determining that the differential echo-train includes a short-$T_2$ porosity fraction that is greater than a threshold value; and inverting two echo trains into two $T_2$ distributions, the two echo trains selected from the long-wait-time echo train, the short-wait-time echo train and the differential echo train, calculating at least two porosity fractions for each of the two $T_2$ distributions, estimating a shift of a porosity amount between the at least two porosity fractions, and detecting the motion artefact based on the shift.

Embodiment 2

The apparatus of embodiment 1, wherein the at least two porosity fractions include a short-$T_2$ porosity fraction and a long-$T_2$ porosity fraction.

Embodiment 3

The apparatus of embodiment 2, wherein the two $T_2$ distributions include a long-wait-time $T_2$ distribution estimated by inverting the long-wait-time echo train, and a short-wait-time $T_2$ distribution estimated by inverting the short-wait-time echo train.

Embodiment 4

The apparatus of embodiment 2, wherein the two $T_2$ distributions include a long-wait-time $T_2$ distribution estimated by inverting the long-wait-time echo train, and the differential $T_2$ distribution.

Embodiment 5

The apparatus of embodiment 4, wherein the differential $T_2$ distribution is computed by inverting the difference between the long-wait-time echo train and the short-wait-time echo train.

Embodiment 6

The apparatus of embodiment 1, wherein the processor is configured to further perform correcting the NMR measurement data based on the shift.

Embodiment 7

The apparatus of embodiment 6, wherein the correcting is applied to the long-wait-time $T_2$ distribution.

Embodiment 8

The apparatus of embodiment 7, wherein the correcting includes shifting a porosity amount corresponding to the estimated shift from the short-$T_2$ porosity fraction to the long-$T_2$ porosity fraction.

Embodiment 9

The apparatus of embodiment 2, wherein estimating the shift of the porosity amount includes one of: estimating a difference between a first short-$T_2$ porosity fraction from one of the two $T_2$ distributions and a second short-$T_2$ porosity fraction from another of the two $T_2$ distributions; and estimating a difference between the first short-$T_2$ porosity fraction and the second short-$T_2$ porosity fraction, wherein at least one of the first and second short-$T_2$ porosity fractions is multiplied by a factor.

Embodiment 10

The apparatus of embodiment 2, wherein estimating the shift of the porosity amount includes one of: estimating a difference between a first long-$T_2$ porosity fraction from one of the two $T_2$ distributions and a second long-$T_2$ porosity fraction from another of the two $T_2$ distributions; estimating a ratio between the first long-$T_2$ porosity fraction and the second long-$T_2$ porosity fraction; and estimating a difference between the first long-$T_2$ porosity fraction and the second long-$T_2$ porosity fraction, wherein at least one of the first and second long-$T_2$ porosity fractions is multiplied by a factor.

Embodiment 11

A method of performing a nuclear magnetic resonance (NMR) measurement, the method comprising: receiving NMR measurement data including a long-wait-time echo train and a short-wait-time echo train, the measurement data generated by a nuclear magnetic resonance (NMR) measurement device disposed in a carrier in an earth formation, the NMR measurement device including a transmitting assembly configured to emit one or more dual-wait-time pulse sequences into a formation volume of interest; and analyzing the long-wait-time echo train and the short-wait-time echo train by a processor to detect a potential motion artefact related to a magnetic field variation in the volume of interest, wherein analyzing includes at least one of: estimating a difference between the long-wait-time echo train and the short-wait-time echo train to generate a differential echo-train, inverting the differential echo-train into a differential $T_2$ distribution, and detecting the motion artefact in response to determining that the differential echo-train includes a short-$T_2$ porosity fraction that is greater than a threshold value; and inverting two echo trains into two $T_2$ distributions, the two echo trains selected from the long-wait-time echo train, the short-wait-time echo train and the differential echo train, calculating at least two porosity fractions for each of the two $T_2$ distributions, estimating a shift of a porosity amount between the at least two porosity fractions, and detecting the motion artefact based on the shift.

Embodiment 12

The method of embodiment 11, wherein the at least two porosity fractions include a short-$T_2$ porosity fraction and a long-$T_2$ porosity fraction.

Embodiment 13

The method of embodiment 12, wherein the two $T_2$ distributions include a long-wait-time $T_2$ distribution estimated by inverting the long-wait-time echo train, and a short-wait-time $T_2$ distribution estimated by inverting the short-wait-time echo train.

Embodiment 14

The method of embodiment 12, wherein the two $T_2$ distributions include a long-wait-time $T_2$ distribution estimated by inverting the long-wait-time echo train, and the differential $T_2$ distribution.

Embodiment 15

The method of embodiment 14, wherein the differential $T_2$ distribution is computed by inverting the difference between the long-wait-time echo train and the short-wait-time echo train.

Embodiment 16

The method of embodiment 11, further comprising correcting the NMR measurement data based on the shift.

Embodiment 17

The method of embodiment 16, wherein the correcting is applied to the long-wait-time T2 distribution.

Embodiment 18

The method of embodiment 17, wherein the correcting includes shifting a porosity amount corresponding to the estimated shift from the short-$T_2$ porosity fraction to the long-$T_2$ porosity fraction.

Embodiment 19

The method of embodiment 12, wherein estimating the shift of the porosity amount includes one of: estimating a difference between a first short-$T_2$ porosity fraction from one of the two $T_2$ distributions and a second short-$T_2$ porosity fraction from another of the two $T_2$ distributions; and estimating a difference between the first short-$T_2$ porosity fraction and the second short-$T_2$ porosity fraction, wherein at least one of the first and second short-$T_2$ porosity fractions is multiplied by a factor.

Embodiment 20

The method of embodiment 12, wherein estimating the shift of the porosity amount includes one of: estimating a difference between a first long-$T_2$ porosity fraction from one of the two $T_2$ distributions and a second long-$T_2$ porosity fraction from another of the two $T_2$ distributions; estimating a ratio between the first long-$T_2$ porosity fraction and the second long-$T_2$ porosity fraction; and estimating a difference between the first long-$T_2$ porosity fraction and the second long-$T_2$ porosity fraction, wherein at least one of the first and second long-$T_2$ porosity fractions is multiplied by a factor.

In connection with the teachings herein, various analyses and/or analytical components may be used, including digital and/or analog subsystems. The system may have components such as a processor, storage media, memory, input, output, communications link (wired, wireless, pulsed mud, optical or other), user interfaces, software programs, signal processors and other such components (such as resistors, capacitors, inductors, etc.) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user, or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

What is claimed is:

1. A nuclear magnetic resonance (NMR) apparatus for estimating properties of an earth formation, the apparatus comprising:
    a carrier configured to be deployed in a borehole in the earth formation;
    a nuclear magnetic resonance (NMR) measurement device including a transmitting assembly configured to emit one or more dual wait time pulse sequences, and a receiving assembly configured to detect a long-wait-time echo train and a short-wait-time echo train based on the one or more dual-wait-time pulses sequences; and
    a processor configured to analyze the long-wait-time echo train and the short-wait-time echo train to detect a potential motion artifact related to a magnetic field variation in the volume of interest, the processor configured to perform at least one of:
    estimating a difference between the long-wait-time echo train and the short-wait-time echo train to generate a differential echo-train, inverting the differential echo-train into a differential $T_2$ distribution, and detecting the motion artifact in response to determining that the differential echo-train includes a short-$T_2$ porosity fraction that is greater than a threshold value; and
    inverting two echo trains into two $T_2$ distributions, the two echo trains selected from the long-wait-time echo train, the short-wait-time echo train and the differential echo train, calculating at least two porosity fractions for each of the two $T_2$ distributions, estimating a shift of a porosity amount between the at least two porosity fractions of each of the two $T_2$ distributions, and detecting the motion artifact based on the shift.

2. The apparatus of claim 1, wherein the at least two porosity fractions include a short-$T_2$ porosity fraction and a long-$T_2$ porosity fraction.

3. The apparatus of claim 2, wherein the two $T_2$ distributions include a long-wait-time $T_2$ distribution estimated by inverting the long-wait-time echo train, and a short-wait-time $T_2$ distribution estimated by inverting the short-wait-time echo train.

4. The apparatus of claim 2, wherein the two $T_2$ distributions include a long-wait-time $T_2$ distribution estimated by inverting the long-wait-time echo train, and the differential $T_2$ distribution.

5. The apparatus of claim 4, wherein the differential $T_2$ distribution is computed by inverting the difference between the long-wait-time echo train and the short-wait-time echo train.

6. The apparatus of claim 1, wherein the processor is configured to further perform correcting NMR measurement data based on the shift, wherein the NMR measurement data includes the long-wait-time echo train and the short-wait-time echo train.

7. The apparatus of claim 6, wherein the correcting is applied to the long-wait-time $T_2$ distribution.

8. The apparatus of claim 7, wherein the correcting includes shifting a porosity amount corresponding to the estimated shift from the short-$T_2$ porosity fraction to the long-$T_2$ porosity fraction.

9. The apparatus of claim 2, wherein estimating the shift of the porosity amount includes one of:
    estimating a difference between a first short-$T_2$ porosity fraction from one of the two $T_2$ distributions and a second short-$T_2$ porosity fraction from another of the two $T_2$ distributions; and
    estimating a difference between the first short-$T_2$ porosity fraction and the second short-$T_2$ porosity fraction, wherein at least one of the first and second short-$T_2$ porosity fractions is multiplied by a factor.

10. The apparatus of claim 2, wherein estimating the shift of the porosity amount includes one of:
    estimating a difference between a first long-$T_2$ porosity fraction from one of the two $T_2$ distributions and a second long-$T_2$ porosity fraction from another of the two $T_2$ distributions;
    estimating a ratio between the first long-$T_2$ porosity fraction and the second long-$T_2$ porosity fraction; and
    estimating a difference between the first long-$T_2$ porosity fraction and the second long-$T_2$ porosity fraction, wherein at least one of the first and second long-$T_2$ porosity fractions is multiplied by a factor.

11. A method of performing a nuclear magnetic resonance (NMR) measurement, the method comprising:
    receiving NMR measurement data including a long-wait-time echo train and a short-wait-time echo train, the measurement data generated by a nuclear magnetic resonance (NMR) measurement device disposed in a carrier in an earth formation, the NMR measurement device including a transmitting assembly configured to emit one or more dual-wait-time pulse sequences into a formation volume of interest; and
    analyzing the long-wait-time echo train and the short-wait-time echo train by a processor to detect a potential motion artifact related to a magnetic field variation in the volume of interest, wherein analyzing includes at least one of:

estimating a difference between the long-wait-time echo train and the short-wait-time echo train to generate a differential echo-train, inverting the differential echo-train into a differential $T_2$ distribution, and detecting the motion artifact in response to determining that the differential echo-train includes a short- $T_2$ porosity fraction that is greater than a threshold value; and inverting two echo trains into two $T_2$ distributions, the two echo trains selected from the long-wait-time echo train, the short-wait-time echo train and the differential echo train, calculating at least two porosity fractions for each of the two $T_2$ distributions, estimating a shift of a porosity amount between the at least two porosity fractions of each of the two $T_2$ distributions, and detecting the motion artifact based on the shift.

12. The method of claim 11, wherein the at least two porosity fractions include a short-$T_2$ porosity fraction and a long-$T_2$ porosity fraction.

13. The method of claim 12, wherein the two $T_2$ distributions include a long-wait-time $T_2$ distribution estimated by inverting the long-wait-time echo train, and a short-wait-time $T_2$ distribution estimated by inverting the short-wait-time echo train.

14. The method of claim 12, wherein the two $T_2$ distributions include a long-wait-time $T_2$ distribution estimated by inverting the long-wait-time echo train, and the differential $T_2$ distribution.

15. The method of claim 14, wherein the differential $T_2$ distribution is computed by inverting the difference between the long-wait-time echo train and the short-wait-time echo train.

16. The method of claim 11, further comprising correcting the NMR measurement data based on the shift.

17. The method of claim 16, wherein the correcting is applied to the long-wait-time $T_2$ distribution.

18. The method of claim 17, wherein the correcting includes shifting a porosity amount corresponding to the estimated shift from the short-$T_2$ porosity fraction to the long-$T_2$ porosity fraction.

19. The method of claim 12, wherein estimating the shift of the porosity amount includes one of:
  estimating a difference between a first short-$T_2$ porosity fraction from one of the two $T_2$ distributions and a second short-$T_2$ porosity fraction from another of the two $T_2$ distributions; and
  estimating a difference between the first short-$T_2$ porosity fraction and the second short-$T_2$ porosity fraction, wherein at least one of the first and second short-$T_2$ porosity fractions is multiplied by a factor.

20. The method of claim 12, wherein estimating the shift of the porosity amount includes one of:
  estimating a difference between a first long-$T_2$ porosity fraction from one of the two $T_2$ distributions and a second long-$T_2$ porosity fraction from another of the two $T_2$ distributions;
  estimating a ratio between the first long-$T_2$ porosity fraction and the second long-$T_2$ porosity fraction; and
  estimating a difference between the first long-$T_2$ porosity fraction and the second long-$T_2$ porosity fraction, wherein at least one of the first and second long-$T_2$ porosity fractions is multiplied by a factor.

* * * * *